United States Patent
Andersen et al.

(10) Patent No.: US 8,805,618 B2
(45) Date of Patent: Aug. 12, 2014

(54) METHOD AND APPARATUS FOR MONITORING OFFSHORE CONTAMINATION

(75) Inventors: Odd Ketil Andersen, Stavanger (NO); Steinar Sanni, Stavanger (NO); Frank Blaker, Tananger (NO); Eirik Sønneland, Tananger (NO)

(73) Assignee: Biota Guard AS, Stavanger (NO)

( * ) Notice: Subject to any disclaimer, the term of this patent is extended or adjusted under 35 U.S.C. 154(b) by 595 days.

(21) Appl. No.: 12/670,640

(22) PCT Filed: Jul. 24, 2008

(86) PCT No.: PCT/GB2008/002542
§ 371 (c)(1), (2), (4) Date: Jun. 28, 2010

(87) PCT Pub. No.: WO2009/013503
PCT Pub. Date: Jan. 29, 2009

(65) Prior Publication Data
US 2010/0274491 A1    Oct. 28, 2010

(30) Foreign Application Priority Data

Jul. 24, 2007 (GB) .................................. 0714442.1

(51) Int. Cl.
*G01V 1/40* (2006.01)
(52) U.S. Cl.
USPC ............. 702/13; 702/19; 702/25; 210/170.11
(58) Field of Classification Search
USPC ............. 702/9, 12–14, 25, 182, 19; 73/53.01, 73/170.29; 166/338, 344, 349; 119/238, 119/421; 210/170.11
See application file for complete search history.

(56) References Cited

U.S. PATENT DOCUMENTS

| 3,770,052 A | 11/1973 | Childers |
| 4,084,543 A | 4/1978 | Pequegnat |

(Continued)

FOREIGN PATENT DOCUMENTS

| DE | 44 43 788 A1 | 6/1995 |
| DE | 198 48 230 A1 | 4/2000 |

(Continued)

OTHER PUBLICATIONS

Syed A.M. Al-Arabi, Contaminant accumulation and Biomarker responses in caged fish exposed to effluents from anthropogenic sources in the Karnaphuly river, Bangladesh, Jan. 26, 2005, Environmental Toxicology and Chemistry, vol. 24, No. 8, pp. 1968-1978.*

(Continued)

*Primary Examiner* — Sujoy Kundu
*Assistant Examiner* — Harun Chowdhury
(74) *Attorney, Agent, or Firm* — Knobbe, Martens, Olson & Bear, LLP (57) ABSTRACT

The invention provides a method of detecting seawater contamination from an offshore hydrocarbon well facility comprising seabed wellheads connected by hydrocarbon conduits to a seabed pipeline head from which a hydrocarbon pipeline leads to a remote hydrocarbon receiving facility, each said wellhead being provided with a protective cover to which is removably attached a sensor unit, each said sensor unit comprising a biological sensor and a data transmitter coupled by a data transmission line to said remote facility, said well facility further comprising a seawater velocity sensor, a seawater conductivity sensor and a temperature sensor also coupled by a data transmission line, wherein data from said data transmission line is analysed to determine indicia of seawater contamination at said well facility and of the seawater flow at said well facility and thereby to provide a signal indicative of seawater contamination above a preselected limit deriving from said well facility.

16 Claims, 5 Drawing Sheets

(56) References Cited

U.S. PATENT DOCUMENTS

| | | | |
|---|---|---|---|
| 4,448,068 A * | 5/1984 | Sutherland et al. | 73/170.29 |
| 4,626,992 A | 12/1986 | Greaves et al. | |
| 4,723,511 A | 2/1988 | Solam et al. | |
| 4,888,703 A | 12/1989 | Baba et al. | |
| 5,010,776 A | 4/1991 | Lucero et al. | |
| 5,140,855 A | 8/1992 | Gruber | |
| 5,469,144 A | 11/1995 | Gradzki et al. | |
| 5,798,222 A | 8/1998 | Goix | |
| 6,058,763 A | 5/2000 | Shedd et al. | |
| 6,119,630 A * | 9/2000 | Lobsiger et al. | 119/238 |
| 6,393,899 B1 | 5/2002 | Shedd et al. | |
| 6,932,542 B2 * | 8/2005 | Chianis et al. | 405/223.1 |
| 7,009,550 B2 | 3/2006 | Moeller-Jensen | |
| 2002/0063629 A1 | 5/2002 | Cbuang | |
| 2003/0211041 A1 | 11/2003 | Ezratty et al. | |
| 2004/0206162 A1 | 10/2004 | Shedd et al. | |
| 2004/0257264 A1 | 12/2004 | Moeller-Jensen | |
| 2005/0189115 A1 * | 9/2005 | Rytlewski et al. | 166/344 |
| 2008/0217022 A1 * | 9/2008 | Deans | 166/338 |
| 2009/0226373 A1 | 9/2009 | Andersen et al. | |
| 2010/0274491 A1 | 10/2010 | Andersen et al. | |

FOREIGN PATENT DOCUMENTS

| | | | |
|---|---|---|---|
| FR | 2 868 446 A | | 10/2005 |
| GB | 2 385 833 A1 | | 9/2003 |
| WO | WO 99/44057 A1 | | 9/1999 |
| WO | WO 2007/086754 | * | 8/2007 |

OTHER PUBLICATIONS

Kenneth S Johnson, Chemical Sensor Networks fo the aquatic environment, Jan. 24, 2007, Chemical Reviews, vol. 107, No. 2, pp. 623-640.*

S.A.M. Al-Arabi, Contaminant accumulation and biomarker responses in caged fish exposed to effluents from anthropogenic sources in the Karnaphuly river, Bangladesh, Environmental Toxicology and Chemistry, vol. 24, No. 8, pp. 1968-1978, 2005.*

Al-Arabi, S. A.M., et al., 2005 "Contaminant Accumulation and Biomarker Responses in Caged Fish Exposed to Effluents from Anthropogenic Sources in the Karnaphuly River, Bangladesh" *Environmental Toxicology and Chemistry* 24:1968-1978.

Borcherding, J. et al. 1997 "Valve movement response of the mussel *Dreissena polymorpha*—the influence of pH and turbidity on the acute toxicity of pentachlorophenol under laboratory and field conditions" *Ecotoxicology* 6: 153-165.

Cairns, J. et al., 1970 "A Preliminary Report on Rapid Biological Information Systems for Water Pollution Control" *Journal WPCF* 42: 685-703.

Chelazzi, G. et al. 2004 "Different cardiac response to copper in limpets from metal polluted and clean shores of Hong Kong" *Marine Environmental Research* 58: 83-93.

Craig, S. et al. 2004 "Behaviour of the three-spined stickleback, *Gasterosteous aculeatus* (*Gasterosteidae*, Teleostei) in the multispecies freshwater biomonitor: a validation of automated recordings at three levels of ammonia pollution" *Water Research* 38: 2144-2154.

De Flora, S. et al., 1993 "Multiple genotoxicity biomarkers in fish exposed in situ to polluted river water" *Mutation Research* 319:167-177.

De Pirro, M. et al. 2001 "Variations in Cardiac Activity Following Acute Exposure to Copper in Three Co-occurring but Differently Zoned Mediterranean Limpets" *Marine Pollution Bulletin* 42:1390-1396.

Englund, V.P. M. et al. 1994 "Field Method for Monitoring Valve Movements of Bivalved Molluscs" *Water Research* 28: 2219-2221.

Foster, R. B. et al., 1978 "Use of Freshwater Mussels to Monitor Point Source Industrial Discharges" *Environmental Science and Technology* 12:958-962.

Gerhardt, A. et al. 1998 "New Online Biomonitoring System for *Gammarus pulex* (L) (Crustacea): In Situ Test Below a Copper Effluent in South Sweden" *Environmental Science and Technology* 32: 150-156.

Gruber, D. et al., 1981 "Industrial Effluent Monitoring Incorporating a Recent Automated Fish Biomonitoring System" *Water, Air and Soil Pollution* 15:471-481.

Israeli-Weinstein, D. et al. 1998 "Behavioral response of carp (*Cyprinus carpio*) to ammonia stress" *Aquaculture* 165: 81-93.

Jenner, H.A. et al. 1989 "A new system for the detection of valve-movement response of bivalves" *Kema Scientific & Technical Reports* 7: 91-98.

Kádár, E. et al. 2001 "Avoidance responses to aluminium in the freshwater bivalve *Anodonta cygnea*" *Aquatic Toxicology* 55: 137-148.

Kramer, K.J.M. et al. 1989 The valve movement response of mussels: a tool in biological monitoring: *Hydrobiologia* 188/189: 433-443.

Lee, P.G. 1995 "A Review of Automated Control Systems for Aquaculture and Design Criteria for Their Implementation" *Aquacultural Engineering* 14: 205-227.

Liao, C. M. et al. 2005 "Risk-based approach to appraise valve closure in the clam *Corbicula fluminea* in response to waterborne metals" *Enviromental Pollution* 135: 41-52.

Markich, S. J. et al. 2000 "Valve movement responses of *Velesunio angasi* (*Bivalvia* Hyriidae) to manganese and uranium: An exception to the free ion activity model" *Aquatic Toxicology* 51: 155-175.

Morgan. E.L. et al. 1989 "Monitoring real-time biological responses to water-quality events from remote data collection platforms and satellite-linkage" *Remote Data Transmission* (*Proceedings of the Vancouver Workshop*) IAHS Publication No. 178: 97-103.

Morgan, E. L. et al., 1978 "Remote Sensing from Automated Biomonitoring Stations: New Developments in Water Quality Management"*ASB Bulletin* 25:46-47.

Nelms, A. S. et al., 1992 "BeRM: Bioelectric Response Monitor" *Proc. Southeast Conference* 1:91-94 IEEE.

Newsletter from RF-Akvamiljø, 2005 News No. 4, pp. 1-4.

Nicholson, S. 1999 "Cytological and Physiological Biomarker Responses from Green Mussels, *Perna viridis* (L.) Transplanted to Contaminated Sites in Hong Kong Coastal Waters" *Marine Pollution Bulletin* 39: 261-268.

Scott, G. R. et al. 2004 "The effects of environmental pollutants on complex fish behaviour: integrating behavioural and physiological indicators of toxicity" *Aquatic Toxicology* 68: 369-392.

Shezifi, Y. et al. 1997 "The electrophysiological response of fish to hypoxia" *Aquacultural Engineering* 16: 253-259.

Sluyts, H. et al. 1996 "A Dynamic New Alarm System for Use in Biological Early Warning Systems" *Enviromental Toxicology and Chemistry* 15: 1317-1323.

Tahedl, H. et al. 2001 "Automated Biomonitoring Using Real Time Movement Analysis of *Euglena gracilis*" *Ecotoxicology and Enviromental Safety* 48: 161-169.

Van Der Schalie, W. et al. 2001 "Using higher organisms in biological early warning systems for real-time toxicity detection" *Biosensors & Bioelectronics* 16: 457-465.

Westlake, G.F. 1975 "Instream Biomonitoring of Industrial Wastewater Effluents" *The Virginia Journal of Science* 26:78.

Xie, Q. et al. 1995 "The Effect of Activity on the Physiological Rates of Two Clam Species, *Tapes Philippinarum* (Adams & Reeve) and *Tapes Decussatus* (Linnaeus)" *Biology and Environment: Proceedings of the Royal Irish Academy* 95B: 217-223.

Blaker, F., "Biota Guard—Real Time Environmental Effect Monitoring System for Offshore Oil & Gas Production and Exploration Operations", dated Jan. 26, 2009.

Pock, et al., "Designing and Building Real Environmental Decision Support Systems", Environmental Modelling & Software, vol. 19, No. 9, pp. 857-873, dated Nov. 21, 2003.

* cited by examiner

METHOD AND APPARATUS FOR MONITORING OFFSHORE CONTAMINATION

CROSS REFERENCE TO RELATED APPLICATIONS

This application is the national phase under 35 U.S.C. §371 of prior PCT International Application No. PCT/GB2008/002542 which has an International filing date of Jul. 24, 2008, designating the United States of America, which claims the benefit of British Application Number 0714442.1 filed on Jul. 24, 2007, the disclosures of which are hereby expressly incorporated by reference in their entirety and are hereby expressly made a portion of this application.

FIELD OF THE INVENTION

The present invention relates to a method of monitoring the water surrounding an offshore hydrocarbon well in order to detect contamination deriving from that well, and additionally to apparatus for use in such a method.

BACKGROUND OF THE INVENTION

In offshore drilling and hydrocarbon recovery there are risks that materials released into the water surrounding the wellhead or the drilling and/or production platform may reach levels at which marine life in the vicinity is endangered. Discharges may be operational or accidental. Thus examples of operational discharges include produced water during the production stage and drilling fluids and cuttings during the drilling stage. Examples of accidental discharges include hydrocarbons, hydraulic fluids, drilling fluids, cuttings and other chemicals. It is important that such discharges do not cause unacceptable water contamination or other environmental effects and so, when unacceptable discharges occur, it is important for the well operator to take action to reduce or stop contaminant release.

Such actions may include shutting down drilling operations, stopping hydrocarbon recovery, replacing or repairing equipment, and so on, all of which are expensive. It is therefore important for the well operator to be able to determine not only that contamination has occurred but also the source, nature and severity of the contamination: thus for example if contamination is as a result of leakage from passing shipping, corrective action by the well operator would be ineffective, and if contamination is below threshold values for severity then corrective action may as yet not be required.

Monitoring of contamination of water masses is well-known; however the prior art is mostly concerned with downstream monitoring of flowing fresh water, monitoring of effluent discharges from factories, and general monitoring of offshore waters. Little attention has been given to the effective monitoring of seawater surrounding offshore hydrocarbon wells in order to detect contamination by the well rather than contamination in the vicinity of the well. There is thus a need for monitoring systems useful in this regard.

SUMMARY OF THE INVENTION

We have found that monitoring of seawater contamination by offshore hydrocarbon wells is best effected by a combination of chemical, physical and biological sensors arranged around the well at the sea bed and, where a sea surface platform is present, a further such combination arranged around the surface structure, submerged but near the water surface. For certain specific operational discharges, it is also desirable to place such sensors at depths appropriate to monitor the expected discharge plume within the water mass.

DETAIL DESCRIPTION OF THE INVENTION

Viewed from one aspect therefore the invention provides a method of detecting seawater contamination from an offshore hydrocarbon well facility comprising a plurality of seabed wellheads connected by hydrocarbon conduits to a seabed pipeline head (e.g. a PLEM) from which a hydrocarbon pipeline leads to a remote hydrocarbon receiving facility, each said wellhead being provided with a protective cover (eg an over-trawlable wellhead protection structure—WHPS) to which is removably attached a sensor unit, each said sensor unit comprising a biological sensor and a data transmitter coupled by a data transmission line to said remote facility, said well facility further comprising a seawater velocity sensor, a seawater conductivity sensor and a temperature sensor also coupled by a data transmission line to said remote facility, wherein data from said data transmission line is analysed to determine indicia of seawater contamination at said well facility and of the seawater flow at said well facility and thereby to provide a signal indicative of seawater contamination above a preselected limit deriving from said well facility.

Viewed from a further aspect the invention provides apparatus for detecting seawater contamination from an offshore hydrocarbon well facility, said apparatus comprising a plurality of removably attached sensor units each attached at the protective cover of a wellhead of said offshore hydrocarbon well facility and each comprising a biological sensor and a data transmitter coupled by a data transmission line to a remote data analysis facility (eg part of a hydrocarbon receiving facility coupled via a hydrocarbon pipeline to a seabed pipeline head (eg a PLEM) at said offshore hydrocarbon well facility), said apparatus further comprising at said offshore hydrocarbon well facility a seawater velocity sensor, a seawater conductivity sensor and a temperature sensor also coupled by a data transmission line to said remote facility, said apparatus optionally and preferably further comprising a computer arranged to analyse data from said data transmission line to determine indicia of seawater contamination at said well facility and of the seawater flow at said well facility and thereby to provide a signal indicative of seawater contamination above a preselected limit deriving from said well facility.

It is particularly preferred that the well facility also comprise a submerged sediment trap.

In a preferred embodiment of the invention, each sensor unit comprises a said seawater velocity sensor, a seawater conductivity sensor and a temperature sensor also coupled by a data transmission line to said remote facility.

In an especially preferred embodiment a further such sensor unit is removably attached at the seabed pipeline head module (i.e. the PLEM).

In a particularly preferred embodiment of the invention, at least one further sensor unit is placed at a seabed location remote from the well facility, e.g. at a distance of 500 to 1000 m from any wellhead, PLEM or pipeline, especially at a distance of 800 to 2000 m. Such "outlier" sensor units may serve to determine a "background" or "control" value for contamination and are desirably placed around the well facility (where at least three outliers are present) or upstream of the well facility in the sense of the normally prevailing seabed current. Data transmission from outliers may be via a data transmission line or more preferably by acoustic transmission from a transmitter at the outlier through the seawater to a receiver coupled to the main data transmission line leading from the PLEM, optionally via an intermediately positioned seabed transceiver. Acoustic transmissions in the method of the invention are preferably non-continuous, e.g. occurring at time intervals of at least 1 hour and up to 24 hours, and preferably are at frequencies in a wavelength band which has little or no effect on whales, in particular frequencies outside the 17 to 43 kHz band, particularly outside the 1 to 100 kHz band.

The biosensors in the sensor units are preferably raised relative to the seabed to reduce the influence of normal dirt-raising seabed currents, e.g. at a minimum height of 1 to 10 m, especially 2 to 5 m above the surrounding seabed. The bottom of the biosensor for these purposes maybe considered to be the lowest portion of the biosensor in which the species being monitored (the "sentinel" species) is contained.

The well facility sensor units may optionally and preferably also include sensors selected from the following:
acoustic sensors (e.g. hydrophones);
mass spectrometers;
NMR spectrometers;
Heart rhythm sensors;
pH sensors;
seawater pressure sensors;
turbidity sensors;
dissolved oxygen sensors;
passive sampling devices;
chlorophyll sensors; and
sediment traps;
in particular one or more of the latter five such sensors.

Passive sampling sensors may be used to detect organic compound contaminants, e.g. aromatic compounds, and generally operate by the use of a semi-permeable membrane which separates the seawater from a solvent in which the organic compounds are soluble. The solvent may be recovered and analysed when the sensors are periodically replaced or, more preferably, a spectrometric device is included which can analyse the solvent for organic compound content in situ, e.g. an infra-red spectrophotometer.

The chlorophyll sensor may be a spectrofluorometer and serves to detect changes in the flora of the body of water surrounding the sensor, e.g. changes in algal content.

The biosensor may be one or more of the many known biosensors which operate by detecting the effect of changes in the seawater on a selected living species, the sentinel species, usually fish or macroinvertebrates (eg shellfish, crustaceans, sea urchins (eg echinodermata), molluscs and fish, especially filter feeding species, and in particular mussels, clams and scallops), for example changes in respiration, pulse (or heart rhythm), gill movement, population density, growth rate, siphon operation, shell movement (e.g. closure and opening), etc. For this purpose, the biosensors will generally include optical recording apparatus, e.g. a camera, and optionally also light sources, e.g. lasers. Such effects are known to be correlatable to changes in chemical and physical environment.

The sentinel species is preferably one suited to the normal (i.e. non-contaminated) environment at the location at which the biosensor is to be deployed, taking into account parameters including depth, temperature, salinity, biomass content of the surrounding water, etc, and one which is responsive to the types of contamination possible in the event of malfunction of the well facility. Typical examples include macroinvertebrate filterfeeders such as mussels, clams, scallops and oysters. The use of such sentinel species in biomonitoring is discussed for example in U.S. Pat. No. 6,119,630 (Lobsiger), U.S. Pat. No. 6,058,763 (Shedd), U.S. Pat. No. 5,798,222 (Goix), and FR-A-2713778 (Pennec) and by Al-Arabi et al in Environmental Toxicology and Chemistry 24:1968-1978 (2005) and Gruber et al in Water, Air and Soil Pollution 15:421-481 (1981), the contents of all of which are incorporated herein by reference.

In the performance of the present invention the use of bivalves, and in particular mussels, clams and scallops, is preferred.

The sentinel species is housed within the biosensor in such a way that it contacts the seawater at the sensor location but is retained within the sensor, e.g. by the use of a cage with a perforated or mesh wall.

Monitoring will typically be to detect movement of the sentinel species within the sensor (e.g. opening or closing of bivalve shells), or localized variations of movement of water within the sensor, or localized changes in water turbidity, or light or sound emissions or reflections by the sentinel species.

All such measurements may be calibrated against equivalent measurements for the same sentinel species under a range of physico-chemical conditions (e.g. temperature, pressure, salinity, microbe content, sediment content, light intensity, etc.) at a series of different pollutant contents and pollutant exposure periods. In this way, the signals from the biosensors may be analysed to determine whether the presence of particular pollutants is likely and whether it is at unacceptably high levels. Setting up a calibration is facilitated by multivariate or principal component analysis which may be used to produce a prediction matrix which can be applied to the data provided by the sensor units.

Certain of the monitored parameters of the sentinel species, e.g. growth, valve gap, heart rate, etc, can be used in existing environmental models such as DREAM (dose-related environmental risk assessment) which are already in use by the oil and gas industry. Data input from the methods of the invention may thus be used to enhance the reliability and accuracy of the results from such models.

While continuous real-time monitoring is possible according to the invention, it will not always be necessary and data sampling may be effected instead at intervals, e.g. of 1 to 48 hours, optionally with data being collected and averaged between sampling times. Desirably however, the sensor units will be arranged to override any temporally spaced sampling should the detected values of the parameters under study fall outside a "normal operating window", i.e. so that leakages may be detected and dealt with promptly.

The data from the sensor units may thus be used to calculate an indication of contamination from the biosensors, and to determine whether the cause is external to the well facility (e.g. by comparison with outliers and comparison between the biosensors taking into account the seawater velocity (i.e. speed and direction in the horizontal plane) and by correction for influence of temperature, pressure, salinity (itself determinable from the detected conductivity), transient biomass (determinable from the detected chlorophyll concentration), and transient turbidity (e.g. due to unduly high seabed turbulence)).

Where external factors cannot be ruled out, data from the passive sampling sensors may be used to increase the degree of confidence in the contamination indication, and if necessary the biosensors may be retrieved, e.g. using submarines such as AUVs and ROVs, so that autopsies, biopsies or other analyses may be performed. Together this can give rapid confirmation that contamination above a preset threshold has occurred or is occurring and as to whether this is attributable to the operation of the well facility. This enables the well operator to take corrective action with a minimum of delay, e.g. by stopping or slowing hydrocarbon production at one or more of the wellheads, by repairing the wellhead equipment responsible for leakage, etc.

In an alternative form, the invention is also suitable for monitoring the operation of an offshore hydrocarbon well facility which includes a surface (i.e. sea-surface) platform, e.g. a floating or static drilling and/or production platform. In this instance however, two arrays of sensor units are required, one at the seabed and one submerged but near the sea surface.

Viewed from this aspect the invention provides a method of detecting seawater contamination from an offshore hydrocarbon well facility comprising a sea surface drilling or production platform (or a combination of such platforms) connected to a seabed wellhead, wherein a first plurality of at least three submerged sensor units is arranged around said platform at a depth of 15 to 50 m and at a distance of 50 to 500 m and a second plurality of at least three sensor units is arranged at the seabed around said wellhead at a distance of 50 to 500 m, each said sensor unit comprising a biological sensor and a data transmitter, said well facility further comprising a submerged sediment trap, a seawater velocity sensor, a seawater conductivity sensor, a seawater temperature sensor, and a data receiver arranged to receive data from said transmitters, in which method data from said receiver is analysed to determine indicia of seawater contamination at said well facility and of the seawater flow at said well facility and thereby to provide a signal indicative of seawater contamination above a preselected limit deriving from said well facility.

Viewed from a still further aspect the invention also provides apparatus for detecting seawater contamination from an offshore hydrocarbon well facility comprising a sea surface drilling or production platform (or a combination of such platforms) connected to a seabed wellhead, said apparatus comprising a first plurality (ie an array) of at least three submerged sensor units arranged around said platform at a depth of 15 to 50 m and at a distance of 50 to 500 m and a second plurality of at least three sensor units arranged at the seabed around said wellhead at a distance of 50 to 500 m, each said sensor unit comprising a biological sensor and a data transmitter, said apparatus further comprising a submerged sediment trap, a seawater velocity sensor, a seawater conductivity sensor, a seawater temperature sensor, and a data receiver arranged to receive data from said transmitters, said apparatus optionally and preferably further comprising a computer arranged to analyse data from said data receiver to determine indicia of seawater contamination at said well facility and of the seawater flow at said well facility and thereby to provide a signal indicative of seawater contamination above a preselected limit deriving from said well facility.

The sensor units of the first array are preferably buoyant, or attached to a buoy, and connected to a seabed anchoring device, e.g. by a flexible cable, such that in all predictable weather and sea flow conditions they remain at least 50 m from the closest part of the platform or its connection to the seabed, and such that except in extreme weather or sea flow conditions they remain no more than 600 m from such closest parts. The units are submerged, that is to say no part, including any other connected parts, is at or above the sea surface except in storm conditions, e.g. a storm force of 8 or above on the Beaufort scale. Typically anchoring will be such that under calm conditions all parts are at least 15 m below the sea surface and the base of the biosensor is no more than 50 m below sea surface.

The sensor units of the second array are preferably located such that the biosensors are at a height of 1 to 10 m, especially 2 to 5 m, above the surrounding seabed. They may be fixed, e.g. mounted on rigid supports, or alternatively they too may be buoyed or buoyant and tethered to a seated anchoring device. These sensor units are preferably located between 50 and 500 m from the nearest platform support, wellhead or seabed pipeline. Further seabed sensor units, "inliers", may if desired be placed between wellheads or within the area defined by three or more wellheads.

The two arrays preferably each comprise at least 4, especially at least 6, e.g. up to 30, sensor units spaced apart by no more than 100° from a central vertical axis, e.g. an axis through the platform, wellhead or wellhead cluster. The sensor spacing may be uneven, e.g. with sensor units being more densely clustered downstream than upstream (with regard to the dominating current direction) of the platform or, respectively, the wellhead(s).

Besides the first and second sensor unit arrays and any inlier sensor units, outlying submerged but near surface sensor units and outlying seabed sensor units, e.g. at a distance of 500 to 10000 m, especially 800 to 2000 m, are also preferably present, again to provide background or control values for contamination. These again may be around the platform or wellhead(s) or upstream as discussed earlier.

Still further sensor units, "platform sensor units", may if desired be placed on the seabed-to-platform supports of a fixed platform. In this case such platform sensor units may contain physical and/or chemical sensors only, e.g. seawater velocity sensors. Again velocity in this instance may be approximated by horizontal flow rates and velocities.

Where seabed sensor units can be attached to or located within existing subsea structures, this will generally be preferred as such sensors need not then be provided with trawl protection structures.

It is preferred that the submerged but near surface sensor units comprise seawater velocity, seawater conductivity and temperature sensors and optionally but preferably one or both of pressure and chlorophyll sensors. Further sensors of the types already described may also be included.

It is preferred that the seabed sensor units comprise sensors of the types already described for the well facilities having no surface platforms, especially sediment traps.

Data transmission from the sensor units of the first array and the near-surface outliers may be via a data transmission line, e.g. an electric cable or optical fiber, for example running down the tethers to the seabed. In a preferred embodiment, however, data transmission from such sensor units is by acoustic transmission as discussed above, optionally via intermediate transceivers (again subsurface and for example on buoys tethered to the seabed). The use of acoustic data transmission in this way transforms the sensor unit/tether array from being a potential obstacle for anchor handling and other maintenance activity around the platform or sub-sea installation into a useful grid location system, eg for vehicles such as ROVs and AUVs used in these activities.

Data transmission from the second array of sensor units and the seabed inliers and outliers may again be via a data transmission line or may be by acoustic transmission as described earlier.

Data transmission from platform-mounted sensor units is preferably via a data transmission line to the platform.

It will generally be preferable, wherever possible, to use (e.g. piggy-back upon) communication infrastructure that is already in place for data transmission from the sensor units, especially the seabed units, for example optical fibres or power transmission lines.

Transmitted data is preferably collected at the platform for analysis there or for transmission, e.g. by radio, to a remote computer, e.g. at an onshore facility.

The sensor units are preferably wholly or partially dismountable, e.g. using ROVs or AUVs, for replacement of sensors, e.g. for analysis at remote locations as discussed above.

Data analysis and signal/indicia generation may be effected analogously to data analysis for the surface-platform-free well facilities discussed above.

The sensor units, as mentioned above, may include acoustic sensors such as hydrophones. Such acoustic sensors are particularly useful in detecting leakages from subsea frames or installations.

It will be appreciated that, besides the sensor units required for the methods of the invention to incorporate biosensors, the overall set of sensor units used in the methods may include sensor units which do not contain biosensors, for example because they are located at depths at which it is difficult to maintain the sentinel species alive.

Advantageously, the contamination levels before, or at the onset of monitoring using the methods of the invention may be measured and used as a baseline so that monitoring alerts the operators to variations relative to the baseline values or so as to more readily highlight contamination events occurring during monitoring. Likewise, if monitoring according to the invention is for a limited period only, e.g. during a high risk operation, determination of contamination levels before and after the monitoring period may more effectively pinpoint contamination events occurring during monitoring. Such contamination determination may of course be effected with sentinel species and/or by chemical analysis in situ or at a remote location (e.g. a laboratory) and/or by determination of biological effect at such a remote location.

Desirably the data collected by the methods of the invention are correlated to the same time-line so as to improve the cause/effect analysis.

By well facility, it should be noted, is meant herein a facility having a hydrocarbon well in preparation, in operation, or in shutdown mode.

In an especially preferred embodiment, the data set for analysis according to the invention includes weather data and vessel movement data, e.g. data supplied to the analyser by an external source such as a weather bureau or a shipping monitoring bureau, or data collected at the offshore installation using conventional weather monitoring devices (for example for wind speed, air temperature, air pressure, humidity, visibility, light intensity, etc) or vessel detection apparatus, e.g. radar. In this way, causes of variation in the sensor signals which are extraneous to the operation of the offshore installation may more easily be identified and the frequency of "false positive" alerts reduced.

Figure 1:
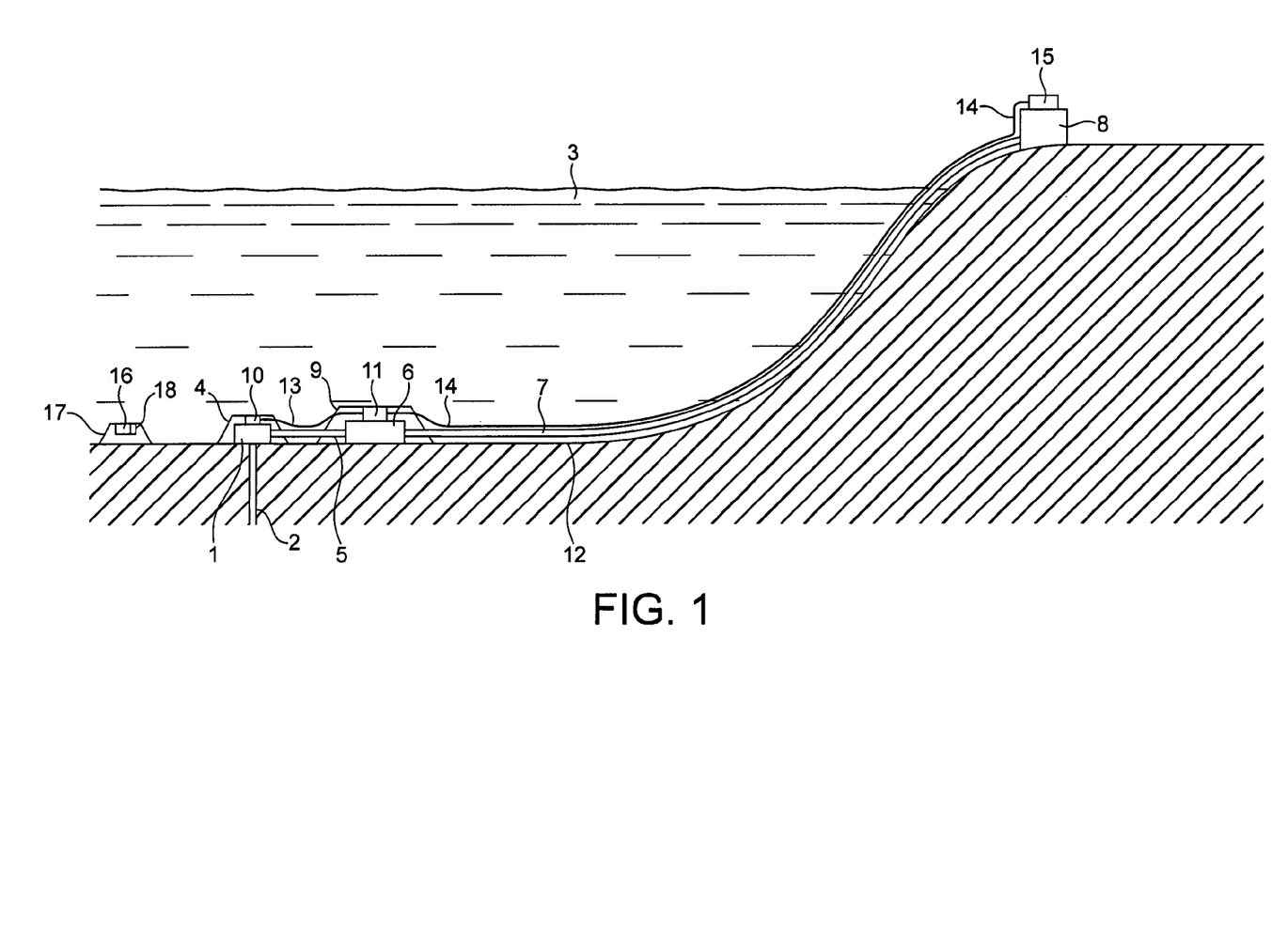
FIG. 1 is a schematic horizontal view of the first well facility having apparatus according to the invention.
Figure 2:
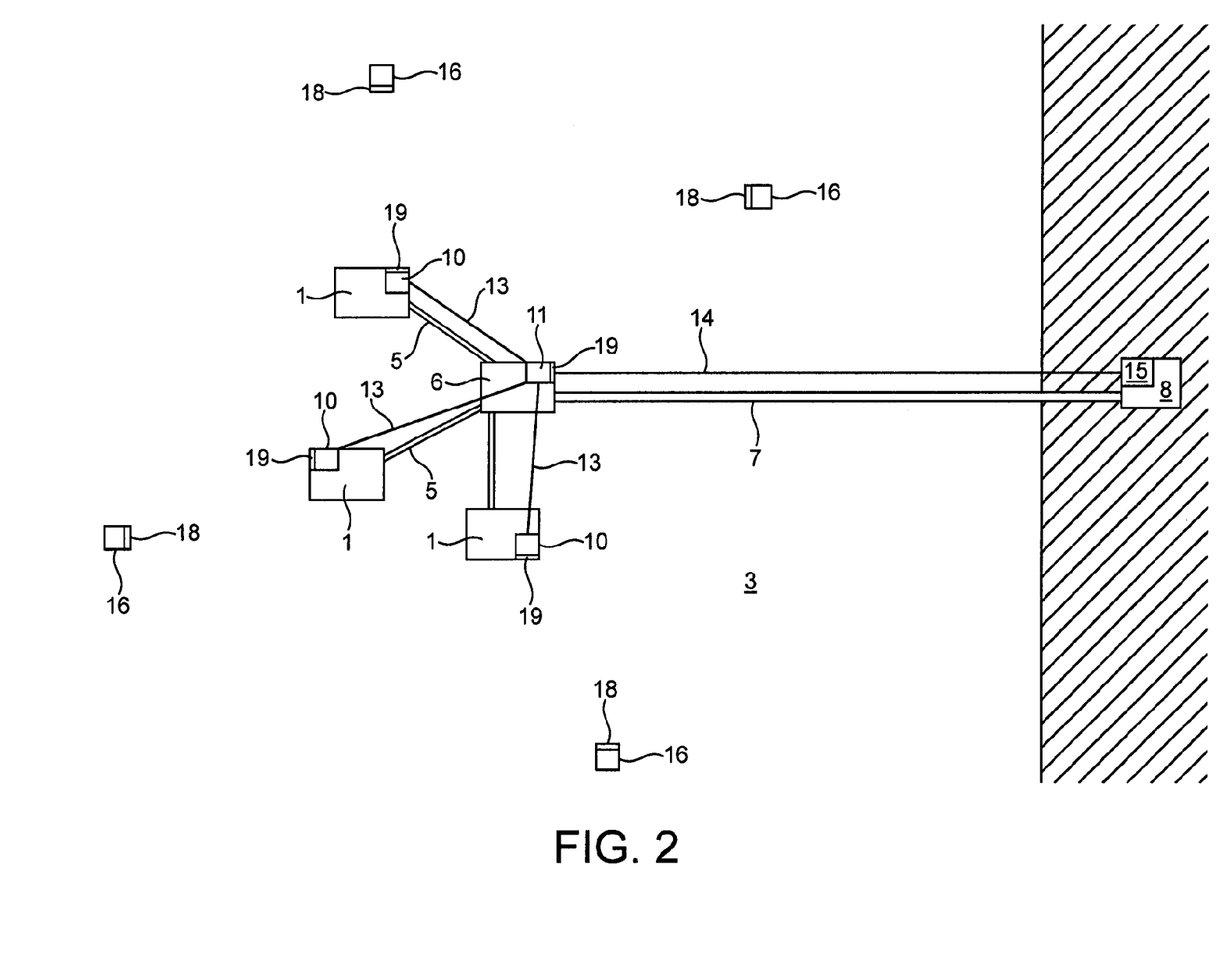
FIG. 2 is a schematic view from above of a well facility as in FIG. 1.
Figure 3:
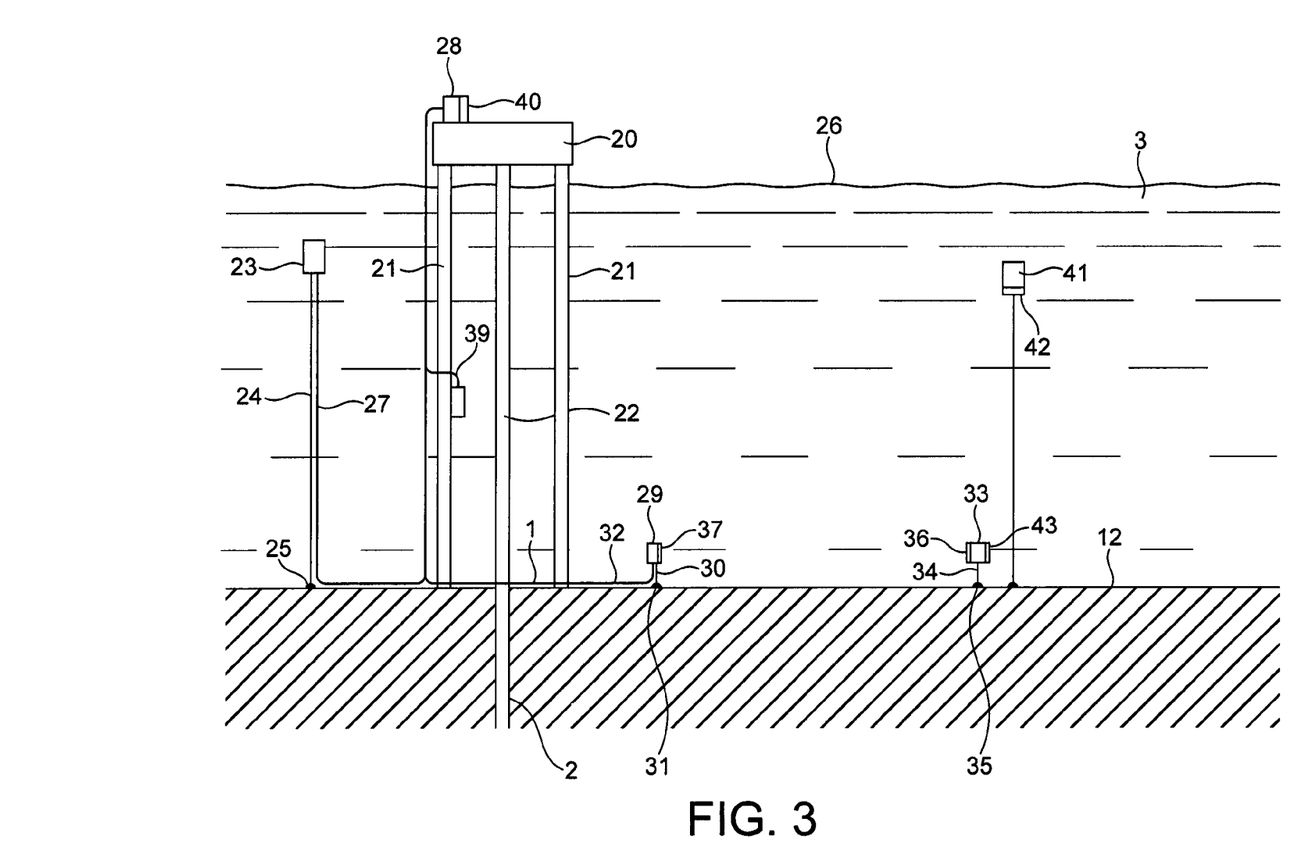
FIG. 3 is a schematic horizontal view of a second well facility having apparatus according to the invention.
Figure 4:
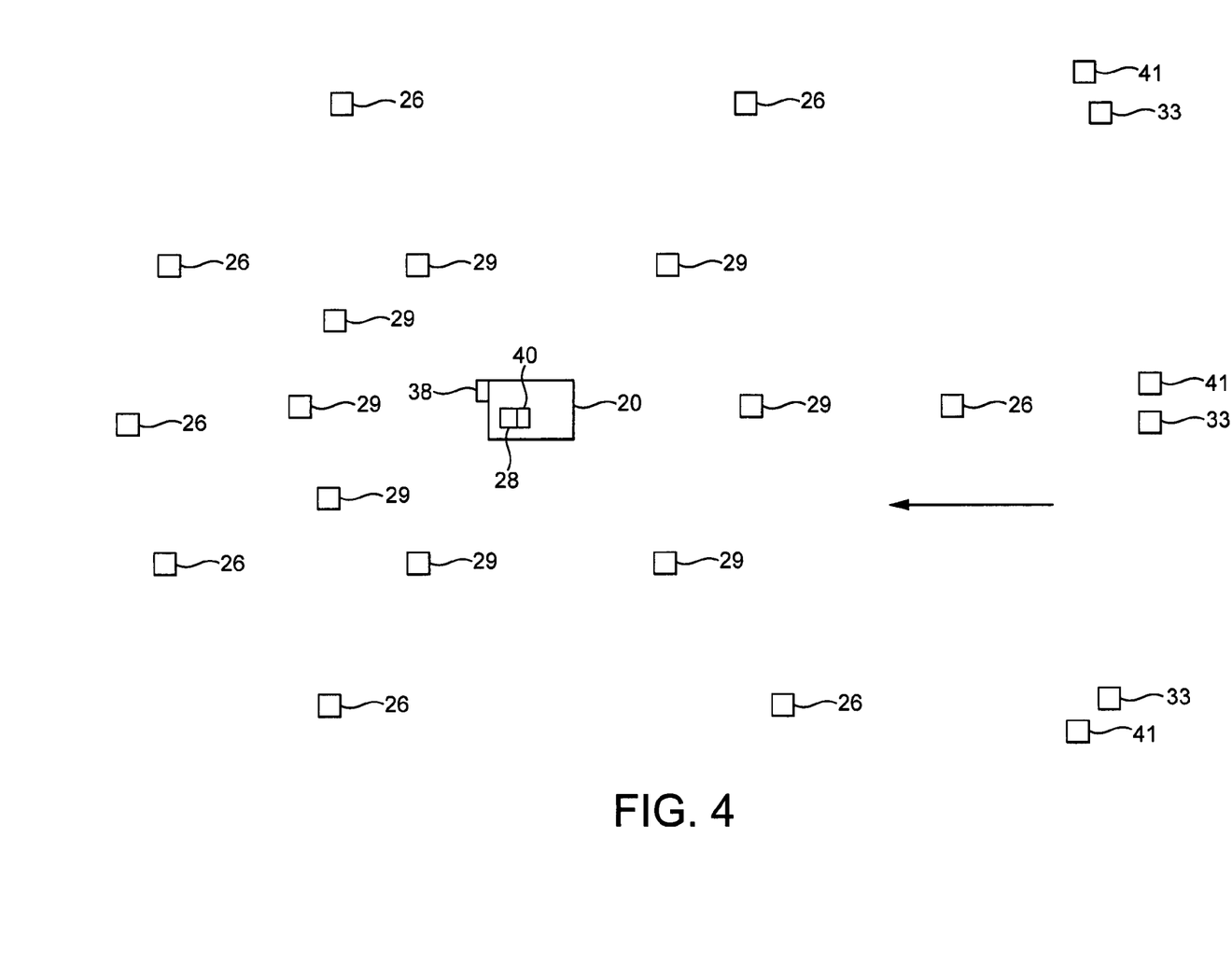
FIG. 4 is a schematic view from above of a well facility as in FIG. 3.

Preferred embodiments of the present invention will now be described by reference to the accompanying drawings, in which:

FIG. 1 is a schematic horizontal view of a first well facility having apparatus according to the invention;

FIG. 2 is a schematic view from above of a well facility as in FIG. 1;

FIG. 3 is a schematic horizontal view of a second well facility having apparatus according to the invention;

FIG. 4 is a schematic view from above of a well facility as in FIG. 3; and

Figure 5:
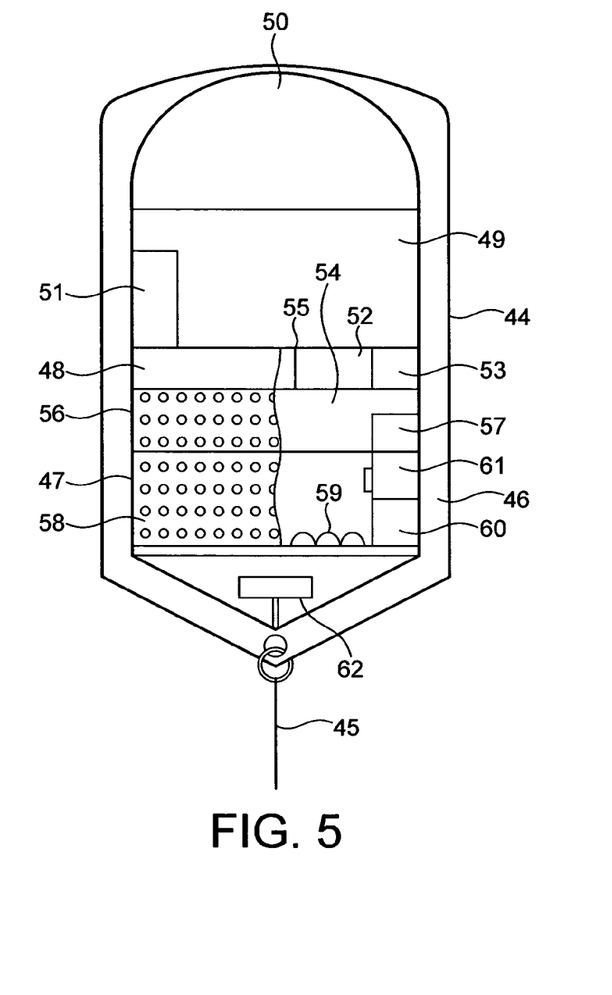
FIG. 5 is a schematic side-on view of a sensor unit usable according to the invention.

FIG. 5 is a schematic side-on view of a sensor unit usable according to the invention.

Referring to FIG. 1 there is shown a wellhead 1 of a hydrocarbon well 2 under seawater 3. Wellhead 1 is provided with a protective cage 4 (an over-trawlable WHPS) to prevent damage by trawling nets and feeds hydrocarbon into minor pipeline 5. Hydrocarbon minor pipeline 5 and similar lines from several other wellheads (not shown) feed hydrocarbon to a pipeline end module (PLEM) 6 which combines the flow and feeds it into major pipeline 7 which leads to a remote onshore receiving facility 8. PLEM 6 is also provided with a protective cage 9 and sensor units 10 and 11 are respectively mounted within cages 4 and 9 at a minimum height of 2 m above the seabed 12. Data transmission lines 13 and 14 lead from the wellhead and PLEM to a data analyser unit 15 at the onshore facility.

At a distance of 300 m from wellhead 1 is a further sensor unit 16 similarly mounted within a protective cage 17 and provided with an acoustic data transmitter 18 for transmission of data to an acoustic receiver 19 on sensor unit 10.

Referring to FIG. 2, there is shown an array of sensor units 10 on a set of wellheads 1 around PLEM 6 and a further array of outlier sensor units 16. In this figure, cages 4, 9 and 17 are not shown.

Referring to FIG. 3 there is shown a static drilling and/or production platform 20 having legs 21 to seabed 12. Drill string 22 leads via wellhead 1 to hydrocarbon well 2.

A buoyant submerged sensor unit 23 is tethered by cable 24 to seabed anchor 25 such that it is 30 m below the sea surface 24 and 100 m from legs 21. Data transmission line 27 leads from sensor unit 23 down cable 24, across seabed 12, and up leg 21 to a data collection unit 28.

A seabed sensor unit 29 is tethered by cable 30 to seabed anchor 31 such that it is 2 m above the seabed and 60 m from legs 21. Data transmission line 32 leads from sensor unit 29 down cable 30, across seabed 12 to join with data transmission line 27.

An outlier seabed sensor unit 33 is tethered by cable 34 to seabed anchor 35 such that it is 2 m above the seabed and 800 m from legs 21. Sensor unit 33 is provided with an acoustic transmitter 36 to transmit data to acoustic receiver 37 on sensor unit 29.

A further sensor unit 38 is attached to leg 21 and is provided with a data transmission line 39 which joins data transmission line 27.

A near-surface buoyant outlier sensor unit 41 is tethered as for sensor unit 23 but 800 m from leg 21. This sensor unit is provided with acoustic transmitter 42 which transmits data to acoustic receiver 43 on seabed outlier sensor unit 38.

Data collected by collection unit 28 is transmitted by radio transmitter 40 to a remote data analyser (not shown).

Referring to FIG. 4, there is shown from above the drilling and/or production platform 20, the first array of submerged near-surface sensor units 26, the second array of seabed sensor units 29, outlier submerged near-surface sensor units 41, and outlier seabed sensor units 33. The arrow indicates the "normal" seawater current direction.

Referring to FIG. 5, there is shown a sensor unit 44 attached to the seabed via cable 45 and comprising a frame 46 carrying four compartments 47, 48, 49 and 50. Compartment 50 is a sealed gas-containing buoyancy tank. Compartment 49 is a sealed unit containing a data receiver (not shown) and carrying on its exterior an acoustic data transmitter 51. Compartment 48 (shown partly cut away) is a detachable two compartment tank in which upper sealed compartment 52 is filled with an organic solvent, contains an infra-red spectrophotometer 53, and is separated from lower compartment 54 by a semi-permeable membrane 55 through which organic compounds may pass. Lower compartment 54 has a perforated peripheral wall 56 and contains a temperature sensor 57.

Compartment 47 (also shown partly cut away) is also detachable and has a perforated peripheral wall 58 and contains mussels 59 as the monitored biological species. The mussels are illuminated by light source 60 and monitored by camera 61.

The compartments may alternatively be arranged so that samples of the sentinel species or samples from passive sampling devices may be removed while the compartments remain in situ.

Below compartment 47 is mounted a flow meter 62 which is freely rotatable about a vertical axis and which is provided with a solid state compass (not shown) so that flow direction is also measured.

What is claimed is:

1. A method of determining whether a source of seawater contamination is from an offshore hydrocarbon well facility or whether the source of the contamination is external to the offshore hydrocarbon well facility, the facility comprising:
   a plurality of seabed wellheads connected by hydrocarbon conduits to a seabed pipeline head from which a hydrocarbon pipeline leads to a remote hydrocarbon receiving facility, each said wellhead being provided with a protective cover to which is removably attached a sensor unit, each said sensor unit comprising a biological sensor and a data transmitter coupled by a data transmission line to said remote facility, said well facility further comprising a seawater velocity sensor, a seawater conductivity sensor and a temperature sensor also coupled by a data transmission line to said remote facility, wherein the method comprises:
   analyzing data from said data transmission line to determine indicia of seawater contamination at said well facility and of the seawater flow at said well facility; and
   providing a signal indicative of seawater contamination above a preselected limit,
   wherein the source of the seawater contamination is determined to be from the offshore hydrocarbon well facility or external to the offshore hydrocarbon well facility based on the seawater flow.

2. The method as claimed in claim 1, wherein each said sensor unit comprises a said seawater velocity sensor, a seawater conductivity sensor and a temperature sensor also coupled by a data transmission line to said remote facility.

3. The method as claimed in claim 1 wherein a further sensor unit is removably attached at a seabed pipeline head module.

4. The method as claimed in claim 1 wherein at least one further sensor unit is placed at a seabed location at a distance of 500 to 1000 m from any wellhead, PLEM or pipeline.

5. The method as claimed in claim 1 wherein said sensor units comprise at least one sensor selected from the group consisting of: pH sensors; seawater pressure sensors; turbidity sensors; dissolved oxygen sensors; passive sampling devices; chlorophyll sensors; and sediment traps.

6. Apparatus for determining whether a source of seawater contamination is from an offshore hydrocarbon well facility or whether the source of the contamination is external to the offshore hydrocarbon well facility, said apparatus comprising a plurality of removably attached sensor units each attached at the protective cover of a wellhead of said offshore hydrocarbon well facility and each comprising a biological sensor and a data transmitter coupled by a data transmission line to a remote data analysis facility, said apparatus further comprising at said offshore hydrocarbon well facility a seawater velocity sensor, a seawater conductivity sensor and a temperature sensor also coupled by a data transmission line to said remote facility, said apparatus further comprising a computer arranged to analyze data from said data transmission line to determine indicia of seawater contamination at said well facility and of the seawater flow at said well facility, and thereby to provide a signal indicative of seawater contamination above a preselected limit, wherein the source of the seawater contamination may be determined to be from the offshore hydrocarbon well facility or external to the offshore hydrocarbon well facility based on the seawater flow.

7. A method of detecting seawater contamination from an offshore hydrocarbon well facility using the apparatus of claim 6, the method comprising:
   generating data by detecting one or more parameters with the sensor unit;
   transmitting the data from the sensor unit to the remote facility via the data transmission line; and
   analyzing the data to determine indicia of seawater contamination at said well facility and of the seawater flow at said well facility.

8. The method of claim 7, the method further comprising:
   providing a signal indicative of seawater contamination above a preselected limit deriving from said well facility.

9. A method of detecting seawater contamination from an offshore hydrocarbon well facility comprising a sea surface drilling or production platform connected to a seabed wellhead, wherein a first plurality of at least three submerged sensor units is arranged around said platform at a depth of 15 to 50 m and at a distance of 50 to 500 m and a second plurality of at least three sensor units is arranged at the seabed around said wellhead at a distance of 50 to 500 m, each said sensor unit comprising a biological sensor and a data transmitter, said well facility further comprising a submerged sediment trap, a seawater velocity sensor, a seawater conductivity sensor, a seawater temperature sensor, and a data receiver arranged to receive data from said transmitters, wherein the method comprises analyzing data from said receiver to determine indicia of seawater contamination at said well facility and of the seawater flow at said well facility; and providing a signal indicative of seawater contamination above a preselected limit deriving from said well facility.

10. Apparatus for detecting seawater contamination from an offshore hydrocarbon well facility comprising a sea surface drilling or production platform connected to a seabed wellhead, said apparatus comprising a first plurality of at least three submerged sensor units arranged around said platform at a depth of 15 to 50 m and at a distance of 50 to 500 m and a second plurality of at least three sensor units arranged at the seabed around said wellhead at a distance of 50 to 500 m, each said sensor unit comprising a biological sensor and a data transmitter, said apparatus further comprising a submerged sediment trap, a seawater velocity sensor, a seawater conductivity sensor, a seawater temperature sensor, and a data receiver arranged to receive data from said transmitters, said apparatus optionally and preferably further comprising a computer arranged to analyze data from said data receiver to determine indicia of seawater contamination at said well facility and of the seawater flow at said well facility and thereby to provide a signal indicative of seawater contamination above a preselected limit deriving from said well facility.

11. The apparatus as claimed in claim 10 wherein the sensor units of said first plurality are buoyant or attached to a buoy.

12. The apparatus as claimed in claim 10 wherein the sensor units of said second plurality are located such that the biosensors therein are at a height of 1 to 10 m above the surrounding seabed.

13. The apparatus as claimed in claim 10 wherein a third plurality of submerged but near surface sensor units and a fourth plurality of seabed sensor units are present at a distance of 500 to 10000 m from a platform, each sensor unit in said third and fourth pluralities comprising a biological sensor and a data transmitter.

14. The apparatus as claimed in claim 10 wherein further sensor units are placed on the seabed-to-platform supports of a fixed said platform, said further sensor units containing physical and/or chemical sensors.

15. A method of detecting seawater contamination from an offshore hydrocarbon well facility comprising a sea surface drilling or production platform connected to a seabed wellhead using the apparatus of claim 10, the method comprising:
   generating data by detecting one or more parameters by one or more of said sensor units; and
   analyzing the data to determine indicia of seawater contamination at said well facility and of the seawater flow at said well facility.

16. The method of claim 15, the method further comprising:
   providing a signal indicative of seawater contamination above a preselected limit deriving from said well facility.

* * * * *